(12) United States Patent
Biel et al.

(10) Patent No.: US 11,208,240 B2
(45) Date of Patent: Dec. 28, 2021

(54) FILLING SYSTEM FOR ELECTRONIC SMOKING DEVICES

(71) Applicant: Fontem Holdings 1 B.V., Amsterdam (NL)

(72) Inventors: Stefan Biel, Hamburg (DE); Sebastian Senftleben, Hamburg (DE); Thorben Rehders, Hamburg (DE); Neha Daryani, Hamburg (DE); Vaclav Borkovec, Hamburg (DE)

(73) Assignee: Fontem Holdings 1 B.V., Amsterdam (NL)

( * ) Notice: Subject to any disclaimer, the term of this patent is extended or adjusted under 35 U.S.C. 154(b) by 0 days.

(21) Appl. No.: 17/127,286

(22) Filed: Dec. 18, 2020

(65) Prior Publication Data

US 2021/0107710 A1    Apr. 15, 2021

Related U.S. Application Data

(62) Division of application No. 16/077,026, filed as application No. PCT/EP2017/052989 on Feb. 10, 2017, now abandoned.

(30) Foreign Application Priority Data

Feb. 12, 2016  (EP) ..................................... 16155542

(51) Int. Cl.
*B65D 47/32*          (2006.01)
*B65D 71/50*          (2006.01)
(Continued)

(52) U.S. Cl.
CPC ............ *B65D 47/32* (2013.01); *A24F 40/485* (2020.01); *B65B 3/06* (2013.01); *B65D 47/248* (2013.01);
(Continued)

(58) Field of Classification Search
CPC .... A24F 47/008; A24F 40/485; A24F 15/015; A61M 2209/045; B65D 47/32; B65D 47/248; B65D 71/502; B65B 3/06
(Continued)

(56) References Cited

U.S. PATENT DOCUMENTS 3,115,907 A * 12/1963 Labat ........................ F23Q 2/52
                                                           141/295
3,667,269 A *  6/1972 Bergner ................... B21D 7/06
                                                            72/166

(Continued)

FOREIGN PATENT DOCUMENTS

CN           1312730 A  ‡  9/2001 ............ A61M 15/06
CN           1312730 A       9/2001
(Continued)

*Primary Examiner* — Jessica Cahill
*Assistant Examiner* — Christopher M Afful
(74) *Attorney, Agent, or Firm* — Dykema Gossett PLLC

(57) ABSTRACT

A filling system for an electronic cigarette (10) is disclosed in which a nozzle (38) of a liquid dispenser (80) contains a plunger (62) which is biased by a spring (60) into a closed position in which liquid is prevented from flowing through the nozzle (38). In use the nozzle (38) is inserted into an open end (42) of a liquid reservoir (34) for an electronic cigarette containing an air tube (32). The plunger (62) engages with the end of the air tube (32) blocking the air tube (32) and opening the liquid flow path through the nozzle (38). The arrangement of the plunger (62) and nozzle (38) is such that operation of the plunger (62) only occurs when the nozzle (38) engaged within a liquid reservoir (32). A membrane (96) can be provided to prevent leakage from the liquid reservoir (34) when the nozzle (38) is disengaged.

17 Claims, 8 Drawing Sheets

(51) Int. Cl.
  *B65B 3/06* (2006.01)
  *B65D 47/24* (2006.01)
  *A24F 40/485* (2020.01)
  *A24F 15/015* (2020.01)
  *A24F 40/00* (2020.01)
  *A24F 40/10* (2020.01)

(52) U.S. Cl.
  CPC .......... *B65D 71/502* (2013.01); *A24F 15/015* (2020.01); *A24F 40/00* (2020.01); *A24F 40/10* (2020.01); *A61M 2209/045* (2013.01)

(58) Field of Classification Search
  USPC ...................................................... 222/481.5
  See application file for complete search history.

(56) References Cited

U.S. PATENT DOCUMENTS

| | | | | |
|---|---|---|---|---|
| 4,545,535 A | ‡ | 10/1985 | Knapp | B05B 7/2445 |
| | | | | 137/564.5 |
| 10,279,934 B2 | ‡ | 5/2019 | Christensen | A24F 47/008 |
| 2009/0311389 A1 | ‡ | 12/2009 | Zoss | B65D 71/502 |
| | | | | 426/12 |
| 2014/0355969 A1 | ‡ | 12/2014 | Stern | A24F 47/008 |
| | | | | 392/390 |
| 2015/0282530 A1 | ‡ | 10/2015 | Johnson | A61M 15/06 |
| | | | | 392/38 |
| 2016/0177551 A1 | ‡ | 6/2016 | Li | G01R 33/07 |
| | | | | 137/78.1 |
| 2017/0013880 A1 | ‡ | 1/2017 | O'Brien | A61M 15/06 |

FOREIGN PATENT DOCUMENTS

| | | | | | |
|---|---|---|---|---|---|
| CN | 103750570 A | ‡ | 4/2014 | ........... | A24F 47/008 |
| CN | 103750570 A | | 4/2014 | | |
| CN | 204157649 U | ‡ | 2/2015 | | |
| CN | 204157649 U | | 2/2015 | | |
| CN | 204232297 U | ‡ | 4/2015 | | |
| CN | 204232297 U | | 4/2015 | | |
| CN | 107454883 A | ‡ | 12/2017 | ............ | B65D 47/06 |
| CN | 107454883 A | | 12/2017 | | |
| CN | 110664019 A | ‡ | 1/2020 | ............... | B65B 3/12 |
| CN | 110664019 A | | 1/2020 | | |
| FR | 2657846 A1 | ‡ | 8/1991 | ......... | B65D 47/2075 |
| FR | 2657846 A1 | | 8/1991 | | |

\* cited by examiner

‡ imported from a related application

FILLING SYSTEM FOR ELECTRONIC SMOKING DEVICES

CROSS REFERENCE TO RELATED APPLICATIONS

This application is a division of U.S. application Ser. No. 16/077,026, filed 9 Aug. 2018 (the '026 application); which is the national stage of international application PCT/EP2017/052989, with an international filing date of 10 Feb. 2017 (the '989 application), now expired. The '026 application and the '989 application are both hereby incorporated by reference as though fully set forth herein.

FIELD OF INVENTION

The present invention relates generally to electronic smoking devices and in particular electronic cigarettes. More specifically the present invention relates to filling systems for refilling the reservoir of an electronic smoking device with liquid for vaporization.

BACKGROUND OF THE INVENTION

An electronic smoking device is an electronic device that permits the user to simulate the act of smoking by producing an aerosol mist or vapor that is drawn into the lungs through the mouth and then exhaled. The inhaled aerosol mist or vapor typically bears nicotine and/or other flavorings without the odor and health risks associated with traditional smoking and tobacco products. In use, a user experiences a similar satisfaction and physical sensation to those experienced from a traditional smoking or tobacco product, and exhales an aerosol mist or vapor of similar appearance to the smoke exhaled when using such traditional smoking or tobacco products.

An electronic smoking device, such as an electronic cigarette, typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol which is extracted from the electronic smoking device via an air tube and a mouthpiece by a user sucking on the mouthpiece.

The reservoir may be either a replaceable or refillable container that is coupled to, or located in, the main body of the electronic smoking device and that is typically made of a resilient plastic material such as high-density polypropylene. The reservoir may contain a wicking material in which the liquid is stored or alternatively may just be a storage space without any wicking material. Once the replaceable or refillable reservoir is emptied it must either be replaced or refilled.

Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other electronic cigarettes, a switch is used to power up the electronic cigarette to generate a puff of vapor.

The ingredients of the liquid for producing the aerosol mist or vapor in smoking-substitute devices vary widely, but typically include water and flavorings in a propylene glycol and/or glycerol base. Nicotine may also be included in solutions intended to fulfil a nicotine replacement role, without the harmful products associated with tobacco smoke.

Typically, electronic cigarettes are refilled by removing a mouthpiece from one end of the electronic cigarette to reveal the open end of the refillable reservoir. Liquid for atomization is then dispensed from a dispenser that commonly resembles the small dropper bottles used for dispensing eye drops by dripping liquid from the outlet liquid-dispensing tip of the dispenser into the revealed open end of the reservoir by squeezing the walls of the dispenser.

Existing liquid dispensing systems suffer from a number of drawbacks.

Frequently electronic smoking devices, particularly electronic cigarettes have approximately the same size and shape as a conventional cigarette, typically about 100 mm with a 7.5 mm diameter, although lengths may range from 70 to 150 or 178 mm, and diameters from 5 to 28 mm. This presents a relatively small target for a user when refilling the device.

Furthermore, in many designs of electronic cigarette, the air tube providing a gas passage way between the atomizer and the mouthpiece is located in the center of the reservoir. In such designs, often it is important when refilling the liquid reservoir for users to avoid dripping liquid into the air tube as if such liquid passes down the air tube into the atomizer this floods the atomizer and temporarily stops the device from working. When the device is then operated to clear the misplaced liquid, this often results in leakage as the misplaced liquid finds its way out of the atomizer through the air passage. Clearing the air passage is also often accompanied by a "gurgling" sound and sensation which users find unpleasant. Having to avoid dripping liquid down the air tube further reduces the cross-section of the available target for dripping liquid into the reservoir.

Difficulties in refilling an electronic smoking device may cause users to miss the reservoir causing their fingers holding the electronic smoking device to come into contact with the liquid for atomization. Further liquid may spill from the reservoir prior to the mouthpiece of the device being re-attached closing the open end of the reservoir. Often liquid for atomization is relatively greasy and is impregnated with flavors which makes coming into contact unpleasant and undesirable as the liquid needs to be washed off and odors from the liquid may be retained on the hands. Further there is a risk that users may accidentally ingest the liquid if the liquid is not washed off.

SUMMARY OF THE INVENTION

In accordance with one aspect of the present invention there is provided a nozzle for a liquid dispensing system for transferring liquid into a liquid reservoir of an electronic smoking device. A plunger is provided within a liquid flow path through the nozzle with the plunger being moveable between an open position in which liquid may flow through the liquid flow path and a closed position in which liquid flow through the liquid flow path is restricted with the plunger being biased towards the closed position. The nozzle and plunger are configured so that when the nozzle is inserted into an engagement position within an opening providing access to a liquid reservoir which contains an air tube for extracting vapour from an electronic smoking device, the plunger engages with the air tube and is moved from the closed position to the open position. When located in an engagement position, the plunger diverts liquid flowing via the flow path through said nozzle into the liquid reservoir and away from the air tube. In some embodiments the plunger may be configured to block the air tube to prevent liquid flowing via the flow path though the nozzle from entering the air tube. An indentation operable to receive an air tube when the nozzle is in an engagement position may be provided for this purpose In some embodiments a sealing member may be mounted on the plunger, wherein the sealing member seals the liquid flow path through the nozzle when said plunger is in the closed position.

A further sealing member may be mounted on the nozzle configured to seal an opening providing access to a liquid reservoir when the nozzle is inserted into an opening. The nozzle may be configured so that the sealing member seals the opening when the nozzle is inserted into an opening prior to an air tube engaging with the plunger and moving the plunger into an open position.

A screw thread, bayonet, magnetic, friction fit, push fit or other type of fitting may be provided on the nozzle which matches a corresponding screw thread at the opening providing access to a liquid reservoir. Such a screw thread, bayonet, magnetic, friction fit, push fit or other type of fitting may be positioned on the nozzle so that if the nozzle is inserted into an opening having a matching screw thread, bayonet, magnetic, friction fit, push fit or other type of fitting, the screw threads, bayonet, magnetic, friction fit, push fit or other type of fitting engage each other before the plunger engages with an air tube within the opening.

In some embodiments an air vent may be provided enabling air to vent from a liquid reservoir when the nozzle is in an engagement position. The air vent may form part of the liquid flow path or may be separate from the liquid flow path. The air vent may be a vent to atmosphere. Alternatively, the air vent may be connected to a low pressure reservoir arranged to extract air from the liquid reservoir when the nozzle is in an engagement position. In some embodiments the low pressure reservoir may be activated by movement of the plunger so as to extract air from the liquid reservoir when the plunger moves to the open position and hence actively suck air out of a liquid reservoir as liquid flows into the liquid reservoir via the nozzle.

The nozzle may be attached to a liquid dispenser and used to refill a liquid reservoir accessible via an opening. The opening may be a mouthpiece port operable to receive a mouthpiece configured for extracting vapour via the air tube.

The liquid reservoir may be part of a combined atomizer and liquid reservoir and may be incorporated in an electronic smoking device.

A membrane having one or more slit valves may be provided adjacent the end of the air tube. If such a membrane is provided, when the nozzle is in an engagement position, the membrane may be caused to be deformed opening the slit valves and permitting liquid to flow into the liquid reservoir.

In accordance with another aspect of the present invention there a method of refiling a liquid reservoir of an electronic cigarette is provided comprising: inserting a nozzle into an opening providing access to the liquid reservoir wherein the plunger of the nozzle engages with an air tube accessible via the opening and is moved from a closed position to an open position, the plunger when engaged being such as to divert liquid flowing through the nozzle into the liquid reservoir and away from the air tube.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Prior to describing refilling systems in accordance with embodiments of the present invention, an exemplary electronic smoking device in the form of an electronic cigarette of the type which might be refilled using the described systems will first be described with reference to FIG. 1 which is a schematic cross-sectional illustration of an exemplary electronic cigarette.

Figure 1:
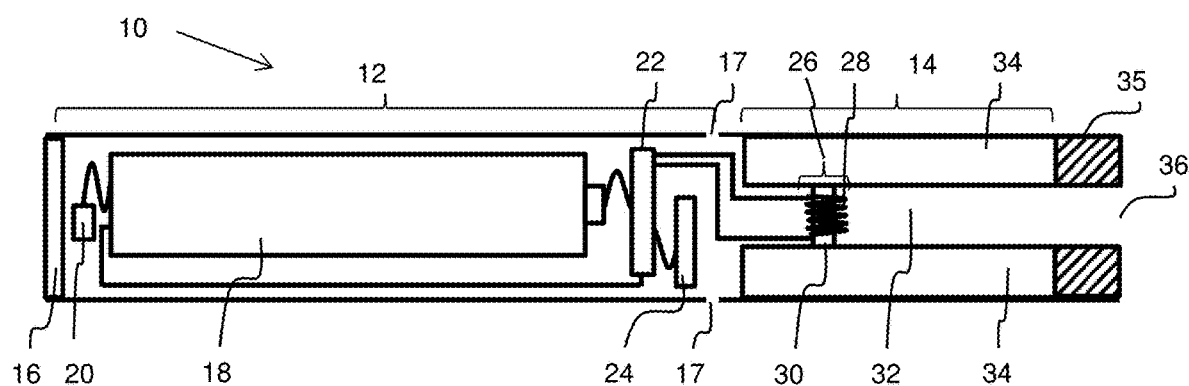
FIG. 1 is a schematic cross-sectional illustration of an exemplary electronic cigarette with a refillable liquid reservoir.

As is shown in FIG. 1, an electronic cigarette 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a power supply portion 12 and an atomizer/liquid reservoir portion 14. Together the power supply portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 178 mm, and diameters from 5 to 28 mm.

The power supply portion 12 and atomizer/liquid reservoir portion 14 are typically made of metal, e.g. steel or aluminum, or of hardwearing plastic and act together with the end cap 16 to provide a housing to contain the components of the electronic cigarette 10. The power supply portion 12 and an atomizer/liquid reservoir portion 14 may be configured to fit together by a friction push fit, a snap fit, or a bayonet attachment, magnetic fit, or screw threads.

The atomizer/liquid storage portion 14 of an electronic cigarette may be removable and/or replaceable from a body portion of an electronic cigarette 10, or may be integrally formed with the body portion of the electronic cigarette 10.

The end cap 16 is provided at the front end of the power supply portion 12. The end cap 16 may be made from translucent plastic or other translucent material to allow a light-emitting diode (LED) 20 positioned near the end cap to emit light through the end cap. The end cap 16 can be made of metal or other materials that do not allow light to pass.

An air inlet may be provided in the end cap 16, at the edge of the inlet next to the cylindrical hollow tube, anywhere along the length of the cylindrical hollow tube, or at the connection of the power supply portion 12 and the atomizer/liquid reservoir portion 14. FIG. 1 shows a pair of air inlets 17 provided at the intersection between the power supply portion 12 and the atomizer/liquid reservoir portion 14.

A power supply, preferably a battery 18, an LED 20, control electronics 22 and optionally an airflow sensor 24 are provided within the cylindrical hollow tube power supply portion 12. The battery 18 is electrically connected to the control electronics 22, which are electrically connected to the LED 20 and the airflow sensor 24. In this example the LED 20 is at the front end of the power supply portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the electronic cigarette 10. The airflow sensor 24 can be any suitable sensor for detecting changes in airflow or air pressure, such as a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across an air tube 32 forming a central passage passing through the atomizer/liquid reservoir portion 14. The coil 28 may be positioned anywhere in the atomizer 26 and may be transverse or parallel to the liquid reservoir 34. The wick 30 and heating coil 28 do not completely block the air tube 32. Rather an air gap is provided on either side of the heating coil 28 enabling air to flow past the heating coil 28 and the wick 30. The atomizer 26 may alternatively use other forms of heating elements, such as ceramic heaters, or fiber or mesh material heaters. Nonresistance heating elements such as sonic, piezo and jet spray may also be used in the atomizer 26 in place of the heating coil.

The air tube 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments the liquid reservoir 34 may comprise a toroidal cavity arranged to be filled with liquid and with the ends of the wick 30 extending into the toroidal cavity.

A mouthpiece 35 having an inhalation port 36 is attached to the end of the atomizer/liquid reservoir portion 14 remote from the end cap 16. The mouth piece 35 acts to enclose the end of the liquid reservoir 34 remote from the end cap 16 with the inhalation port 36 being an extension of the central passage formed by the air tube 32. The mouthpiece 35 and the atomizer/liquid reservoir portion 14 may be configured to fit together by a friction push fit, a snap fit, or a bayonet attachment, magnetic fit, or screw threads.

In use, a user sucks on the electronic cigarette 10. This causes air to be drawn into the electronic cigarette 10 via one or more air inlets, such as air inlets 17, and to be drawn through the air tube 32 towards the air inhalation port 36. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized creating an aerosol (which may comprise gaseous and liquid components) within the air tube 32. As the user continues to suck on the electronic cigarette 10, this aerosol is drawn through the air tube 32 and air inhalation port 36 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol more liquid is drawn into the wick 30 from the liquid reservoir 34 by capillary action and thus is available to be converted into an aerosol through subsequent activation of the heating coil 28.

Of course, in addition to the above description of the structure and function of a typical electronic cigarette 10, variations also exist. For example, the LED 20 may be omitted. The airflow sensor 24 may be placed adjacent the end cap 16 rather than in the middle of the electronic cigarette. The airflow sensor 24 may be replaced with a switch which enables a user to activate the electronic cigarette manually rather than in response to the detection of a change in air flow or air pressure.

Different types of atomizers may be used. Thus for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

First Embodiment

A first embodiment of the present invention will now be described with reference to FIG. 2 which is a perspective view of a nozzle 38 of a liquid dispenser (with the liquid dispenser omitted) and the atomizer/liquid storage portion 14 of an electronic cigarette, and FIGS. 3-5 which are cross sectional views of the nozzle 38 and an end of the atomizer/liquid storage portion 14 in an uncoupled, an intermediate and coupled configuration.

The atomizer/liquid storage portion 14 of an electronic cigarette shown in the figures is shown with the mouthpiece 35 removed. The illustrated features of the atomizer/liquid storage portion 14 of an electronic cigarette comprise a mouthpiece port 39 and a body section 40. The mouthpiece port 39 comprises a hollow section open at both ends and configured to receive an end of a mouthpiece 35 (not shown) in an aperture 42 at a first end thereof. A second aperture 44 at opposite end of mouthpiece port 39 provides fluid communication between the mouthpiece port 39 and both the liquid reservoir 34 and the air tube 32 of the atomizer/liquid storage portion 14 of the electronic cigarette. When a mouthpiece 35 is located within the mouthpiece port 39, the aperture 44 is partly sealed by the end of the mouthpiece 35 to provide fluid communication with the air tube 32 only. This is to prevent liquid contained in liquid reservoir 34 from leaking from the liquid reservoir 34.

During a re-filling process, the mouthpiece 35 is removed from the mouthpiece port 39 of the atomizer/liquid storage portion 14 of the electronic cigarette, leaving the atomizer/liquid storage portion 14 of an electronic cigarette in the state as illustrated.

With the atomizer/liquid storage portion 14 of an electronic cigarette in this state, the nozzle 38 of a liquid dispenser can be slid into the mouthpiece port 39 of the atomizer/liquid storage portion 14 of an electronic cigarette to undertake the re-filling process.

Figure 2:
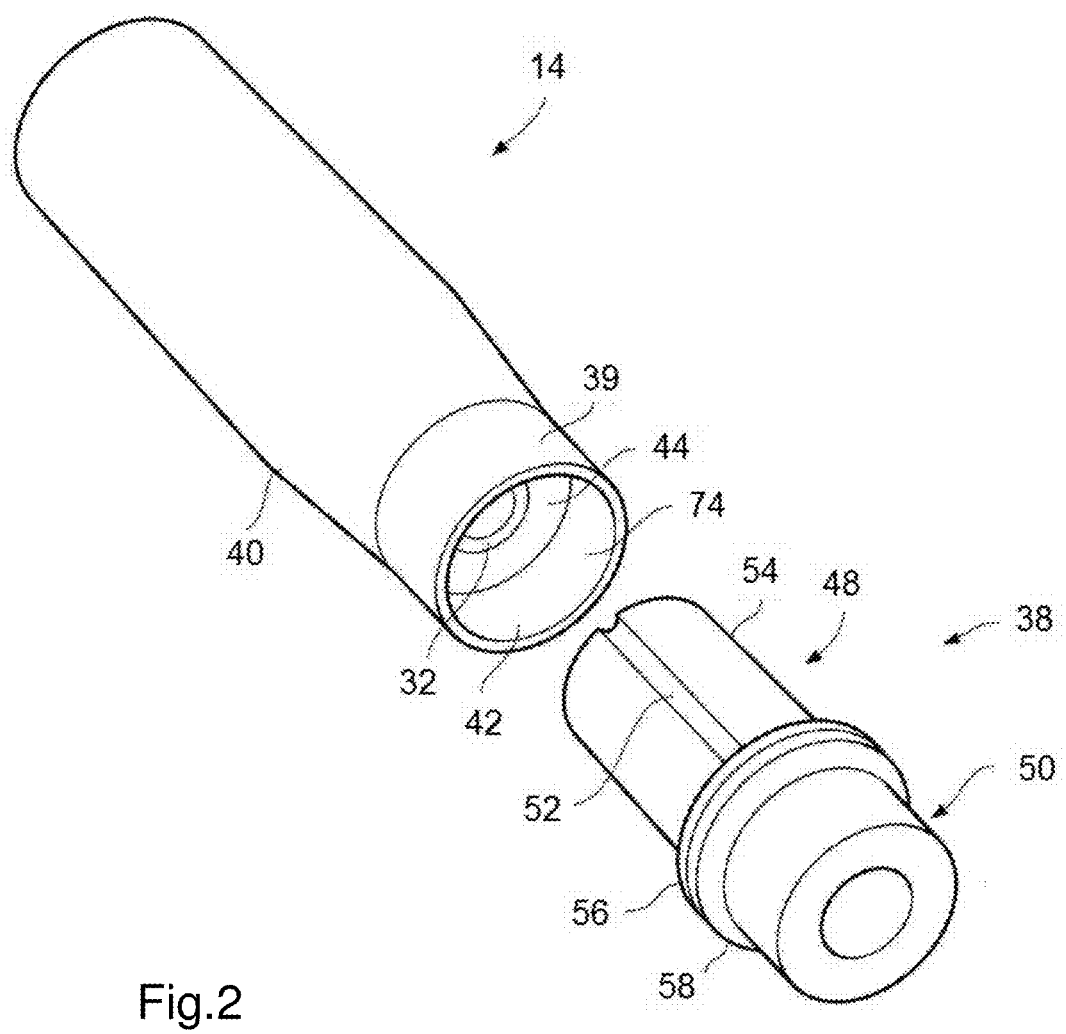
FIG. 2 is a perspective view of a nozzle of a liquid dispenser in accordance with an embodiment of the present invention and an atomizer/liquid storage portion of an electronic cigarette.

Referring first to FIG. 2, which shows the nozzle 38 of a liquid dispenser (the liquid dispenser itself is not shown in FIG. 2) prior to location within the mouthpiece port 39 of the atomizer/liquid storage portion 14, the nozzle 38 in this embodiment comprises a first 48 and a second 50 tubular section joined together. Together the first 48 and second tubular sections act to form a housing and define a liquid flow path through the nozzle 38.

A groove 52 is provided on the exterior wall 54 of the first section 48 of the nozzle 38. Flanges 56,58 extend from the ends of the first section 48 and a second section 50 which abut each other which facilitates joining the sections, together allowing the first 48 and second 50 sections to be manufactured as separate units prior to assembly.

The exterior wall 54 of the first section 48 of the nozzle 38 is slidably engagable within the aperture 42 of the mouthpiece port 39 of the atomizer/liquid storage portion 14 other than the region of the wall 54 comprising the groove 52 which is recessed relative to the size of the aperture 42.

Figure 3:
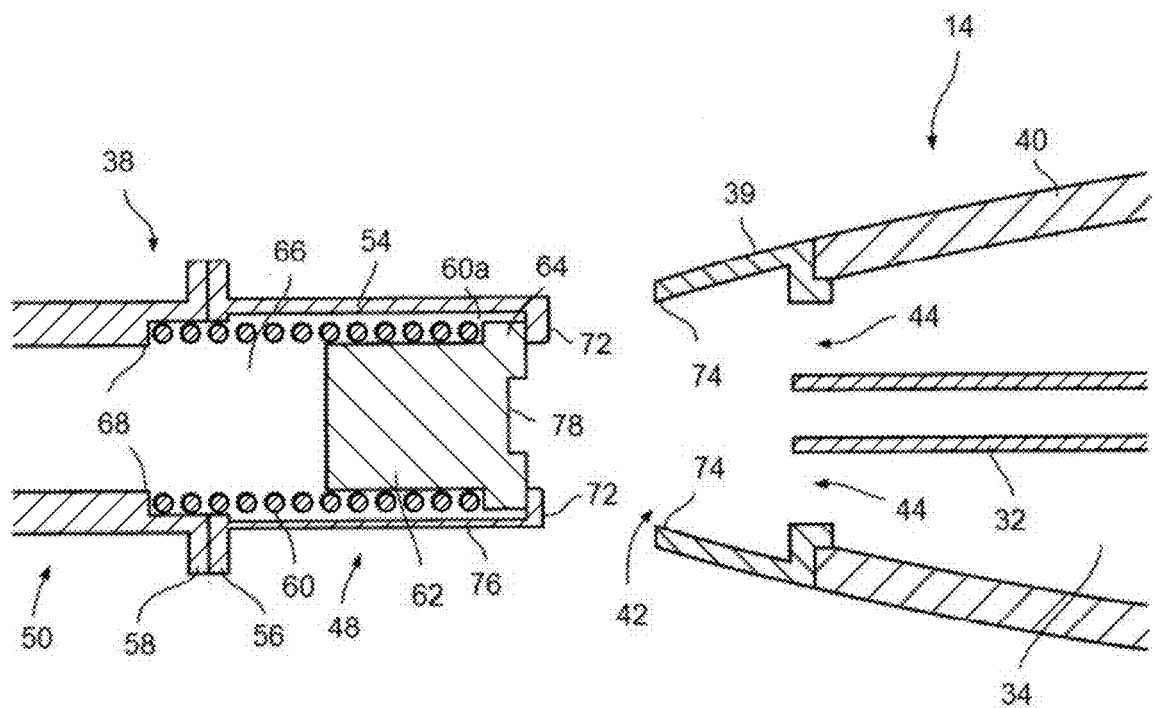
FIG. 3 is a cross-sectional view of the nozzle of a liquid dispenser and the end of the atomizer/liquid storage portion of an electronic cigarette of FIG. 2 in an uncoupled configuration.

Turning now to FIG. 3 which shows a cross-sectional view of the nozzle 38, a helical coil spring 60 is inserted into the cavity of the second section 50 of the nozzle 38 and a plunger 62 extends through the middle of helical coil spring 60 so that shoulder 64 on the plunger 62 may contact an end 60a of the spring 60 The plunger 62 is inserted into the hollow cylindrical cavity 66 of first section 48 of the nozzle 38.

As can be seen in FIG. 3, the first section 48 and second section 50 are connected together so that the spring 60 is partially compressed such that one end, 60a, abuts the shoulder 64 of the plunger 62 and the other end abuts an interior formation 68 of the nozzle 38 (in the illustrated case a formation on second section 50). The compression of the spring 60 causes the plunger 62 to be biased against and abut a partially inwardly extending portion 72 of the first section 48 side wall. The exterior wall 54 of the first section 48 of the nozzle 38 is configured to be in slidable engagement with a portion 74 of the inner wall of mouthpiece port 39 of the atomizer/liquid storage portion 14. Also shown is a thinner section 76 of the exterior wall 54 of the first section of the nozzle 38 which forms the bottom of groove 52 illustrated in FIG. 2.

Figure 4:
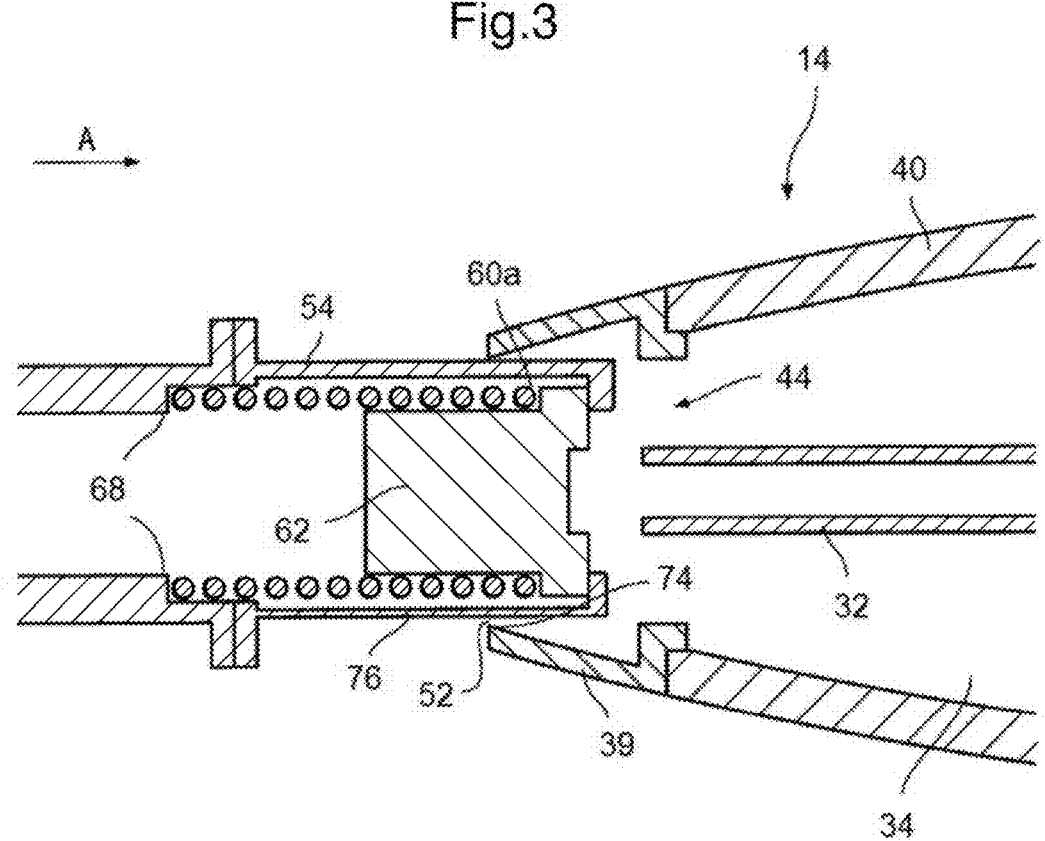
FIG. 4 is a cross-sectional view of the nozzle of a liquid dispenser and the end of the atomizer/liquid storage portion of an electronic cigarette of FIG. 2 in an intermediate stage between an uncoupled configuration and a coupled configuration.

FIG. 4 is a schematic illustration of the nozzle 38 partially inserted into the atomizer/liquid storage portion 14 of an electronic cigarette. Not all reference numerals are shown in this figure for clarity purposes. The slidable engagement of the outer wall 52 of the first section 48 with the portion 74 of the inner wall of the mouthpiece port 39 of the atomizer/liquid storage portion 14 is clearly illustrated. Additionally, groove 52 can be seen to be in the process of being formed between the thinner portion of the wall 54 and the corresponding portion 74 of the inner wall of mouthpiece port 39 of the atomizer/liquid storage portion 14. Advancing the nozzle 38 toward the atomizer/liquid storage portion 14 in a direction indicated by arrow A will bring the nozzle 38 and the atomizer/liquid storage portion 14 closer to full engagement.

Figure 5:
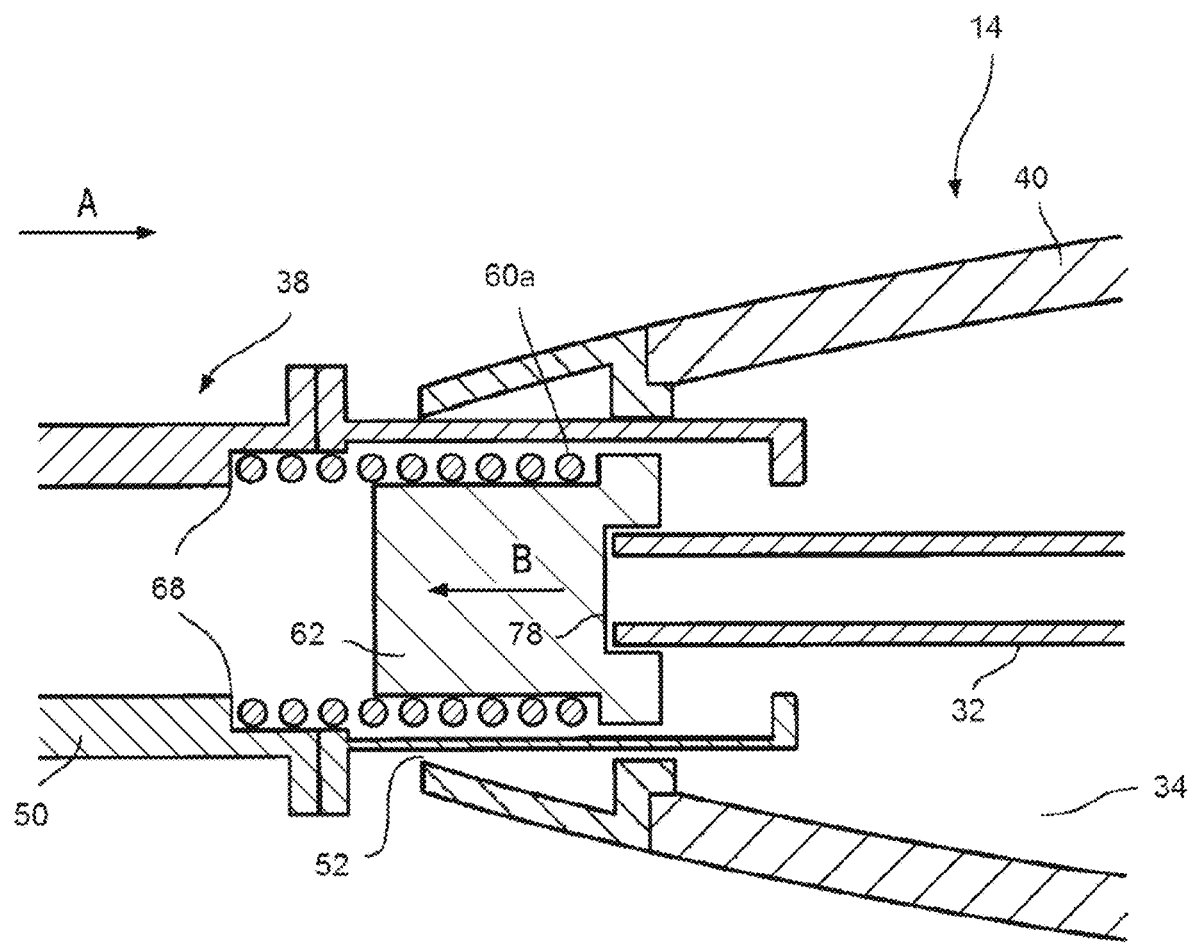
FIG. 5 is a cross-sectional view of the nozzle of a liquid dispenser and the end of the atomizer/liquid storage portion of an electronic cigarette of FIG. 2 in a coupled configuration.

FIG. 5 is an illustration of the nozzle 38 and atomizer/liquid storage portion 14 fully engaged with each other. As can be seen, the travel of first section 48 of the nozzle 38 into the mouthpiece port 39 of the atomizer/liquid storage portion 14 of the electronic cigarette in the direction indicated by arrow A causes a sealing surface 78 of plunger 62 to come into contact with the end of the air tube 32 of the atomizer/liquid storage portion 14 of the electronic cigarette. This forces the plunger 62 back against spring 60. It should be noted that groove 52 extends along wall 54 to form a gas pathway from groove 52 into the liquid reservoir 34. The gas pathway provides a venting mechanism for air to escape from a reservoir being filled with a liquid but also may provide for the ingress of air into a bottle from which the liquid is being supplied to the reservoir.

Forcing the plunger 62 back in this manner (i.e. in the direction indicated by arrow B) causes a gap to open between the shoulder 64 of the plunger 62 and the inwardly extending portion 72 of the first section 48 of the nozzle 38 thereby opening a valve element of the nozzle 38 to provide a liquid pathway through the nozzle 38.

At the same time the sealing surface 78 of the plunger 62 engages with and blocks the open end of the air tube 32. Thus when the valve element of the nozzle 38 is opened to provide a liquid pathway through the nozzle 38, the plunger 62 blocks the open end of the air tube 32 and prevents liquid from entering the air tube 32 and hence prevents liquid from flooding the atomizer 26. In the illustrated embodiment a central portion of the sealing surface 78 is indented so that when the plunger 62 engages the end of the air tube 32, the air tube 32 enters the recess defined by the indentation.

Typically, a re-filling process will be conducted with the nozzle 38 and atomizer/liquid storage portion 14 of an electronic cigarette substantially vertical with the nozzle 38 above the atomizer/liquid storage portion 14 of an electronic cigarette. When held in this manner, liquid to be dispensed will travel in the direction of arrow A under the influence of gravity down through the nozzle 38 and into the liquid reservoir 34 of the atomizer/liquid storage portion 14 of the electronic cigarette.

Figure 6:
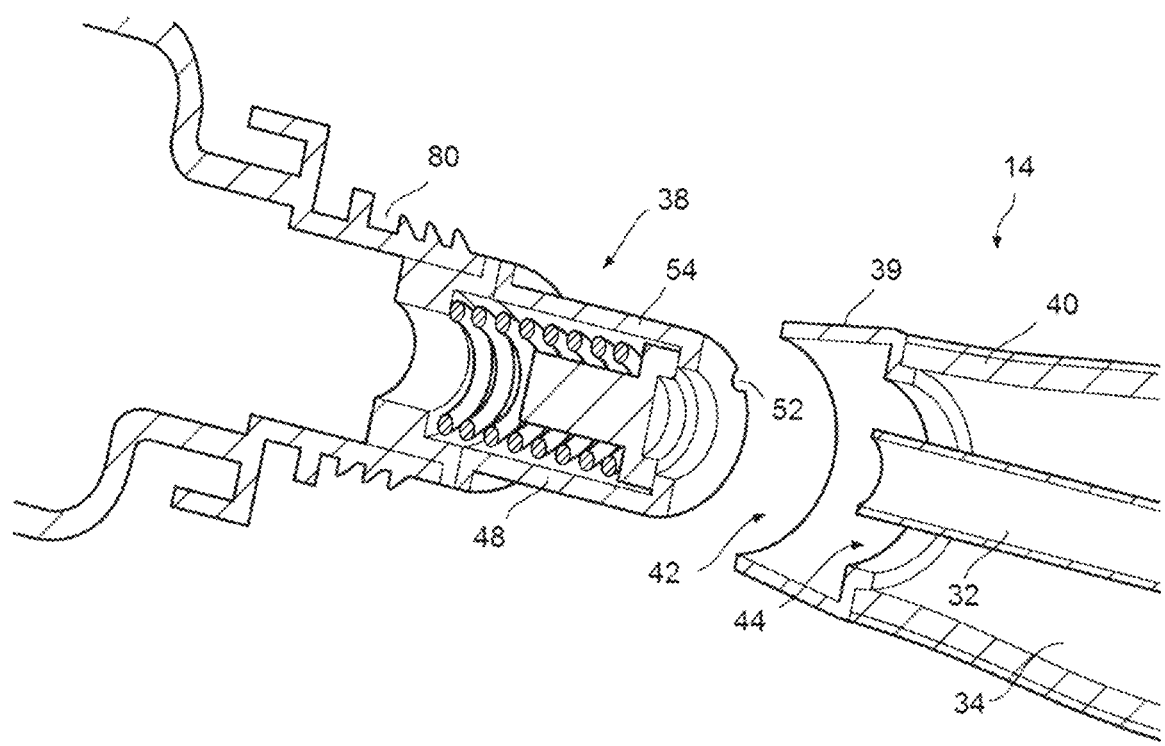
FIG. 6 is another cross-sectional view illustrating the nozzle of the liquid dispenser and the end of the atomizer/liquid storage portion of an electronic cigarette of FIG. 2 in an uncoupled configuration.
Figure 7:
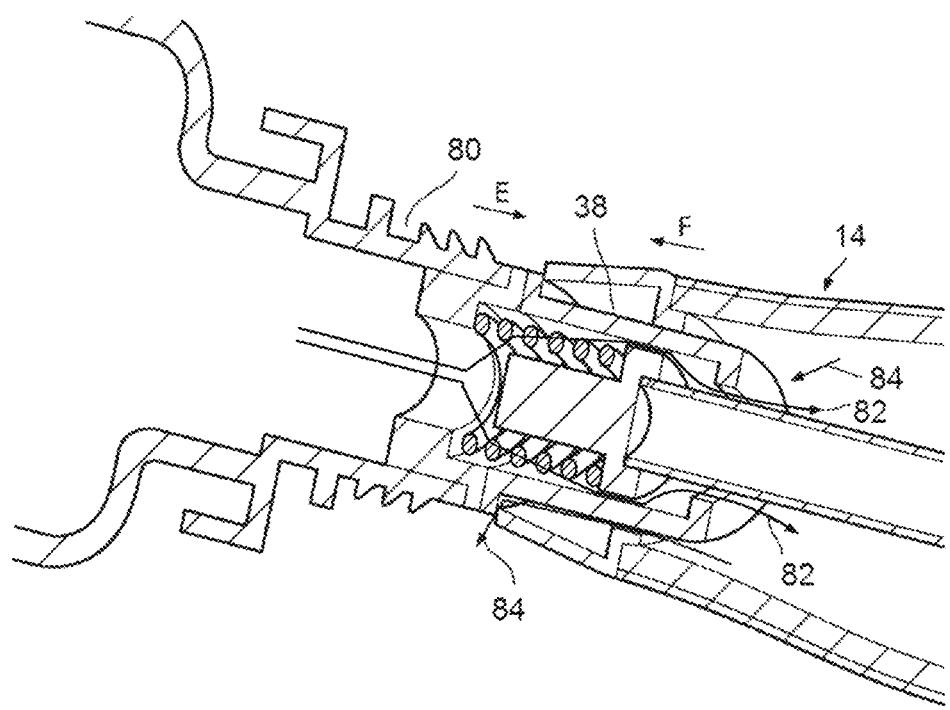
FIG. 7 is a further cross-sectional view illustrating the nozzle of the liquid dispenser and the end of the atomizer/liquid storage portion of an electronic cigarette of FIG. 2 in a coupled configuration.

Turning now to FIGS. 6 and 7, use of the nozzle 38 for dispensing liquid from a bottle into the liquid reservoir 34 of the atomizer/liquid storage portion 14 of an electronic cigarette is illustrated in perspective cross-section in both figures.

FIG. 6 shows the nozzle 38 and atomizer/liquid storage portion 14 of an electronic cigarette in the uncoupled configuration and FIG. 7 shows the nozzle 38 and atomizer/liquid storage portion 14 of an electronic cigarette in the coupled configuration. The nozzle 38 is disposed in the neck of a liquid dispenser bottle 80. Before insertion of the nozzle 38 into the mouthpiece port 39 of the atomizer/liquid storage portion 14 of an electronic cigarette (i.e. as shown in FIG. 6) the plunger 62 of nozzle 38 is in a closed configuration. With the nozzle 38 inserted in the mouthpiece port 39 of the atomizer/liquid storage portion 14 (i.e. as shown in FIG. 7), and upon application of a force denoted by arrow E to dispenser bottle 80 and an oppositely directed force denoted by arrow F to the atomizer/liquid storage portion 14, the plunger 62 is moved into an open position which permits liquid to flow from dispenser bottle 80 to the liquid reservoir 34 of atomizer/liquid storage portion 14 of an electronic cigarette. Liquid flow from the dispenser bottle 80 to the liquid reservoir 34 of atomizer/liquid storage portion 14 of an electronic cigarette is illustrated in FIG. 7 by way of arrows 82.

Gas displaced from the liquid reservoir 34 as a result of the liquid being added is vented from the liquid reservoir 34 via a gas pathway formed by groove 52. Gas flow from the liquid reservoir 34 of atomizer/liquid storage portion 14 of an electronic cigarette is illustrated in FIG. 7 by way of arrows 84.

The displaced gas may, for example, be vented to atmosphere (as shown in FIG. 7). Optionally, the groove 52 may be configured to form a gas pathway for venting the displaced gas into the dispenser bottle 80.

Second Embodiment

A second embodiment of the present invention will now be described with reference to FIGS. 8 and 9 which are cross-sectional views of a nozzle 38 of a liquid dispenser 80 attached to a mouthpiece port 39 at the end of the atomizer/liquid storage portion 14 of an electronic cigarette in a first and a second configuration.

Figure 8:
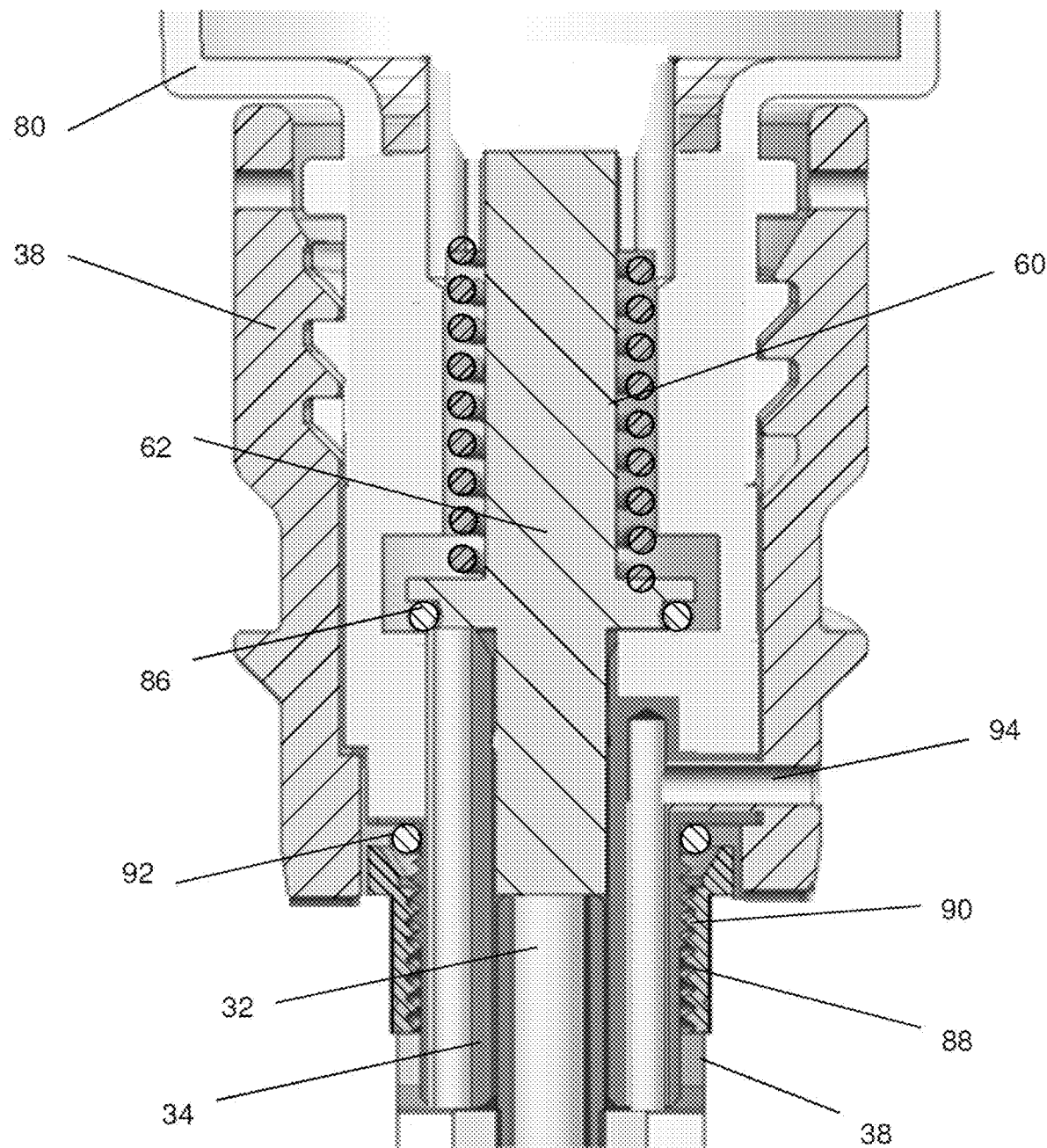
FIG. 8 is a cross-sectional view of a nozzle of a liquid dispenser of a second embodiment connected into a mouthpiece port at the end of the atomizer/liquid storage portion in a first configuration.

As in the first embodiment, in this embodiment a plunger 62 is provided within the nozzle 38 with the plunger 62 being biased in the position illustrated in FIG. 8 by a coil spring 60. In this embodiment portion of the plunger 62 rests against and compresses a seal 86 attached to the plunger 62 which acts to block a liquid flow path and prevent liquid from flowing out of a dispenser bottle 80 to which the nozzle 38 is attached.

In this embodiment a screw thread 88 is provided on the inside wall of the mouthpiece port 39 at the end of the atomizer/liquid storage portion 14 of an electronic cigarette arranged to match with a corresponding screw thread on a mouthpiece (not shown) when the electronic cigarette is in use. A matching screw thread 90 is provided on the exterior wall at the tip of the nozzle 38. A further seal 92 is provided on the nozzle 38 adjacent the end of the screw thread 90 remote from the tip of the nozzle 38.

Figure 9:
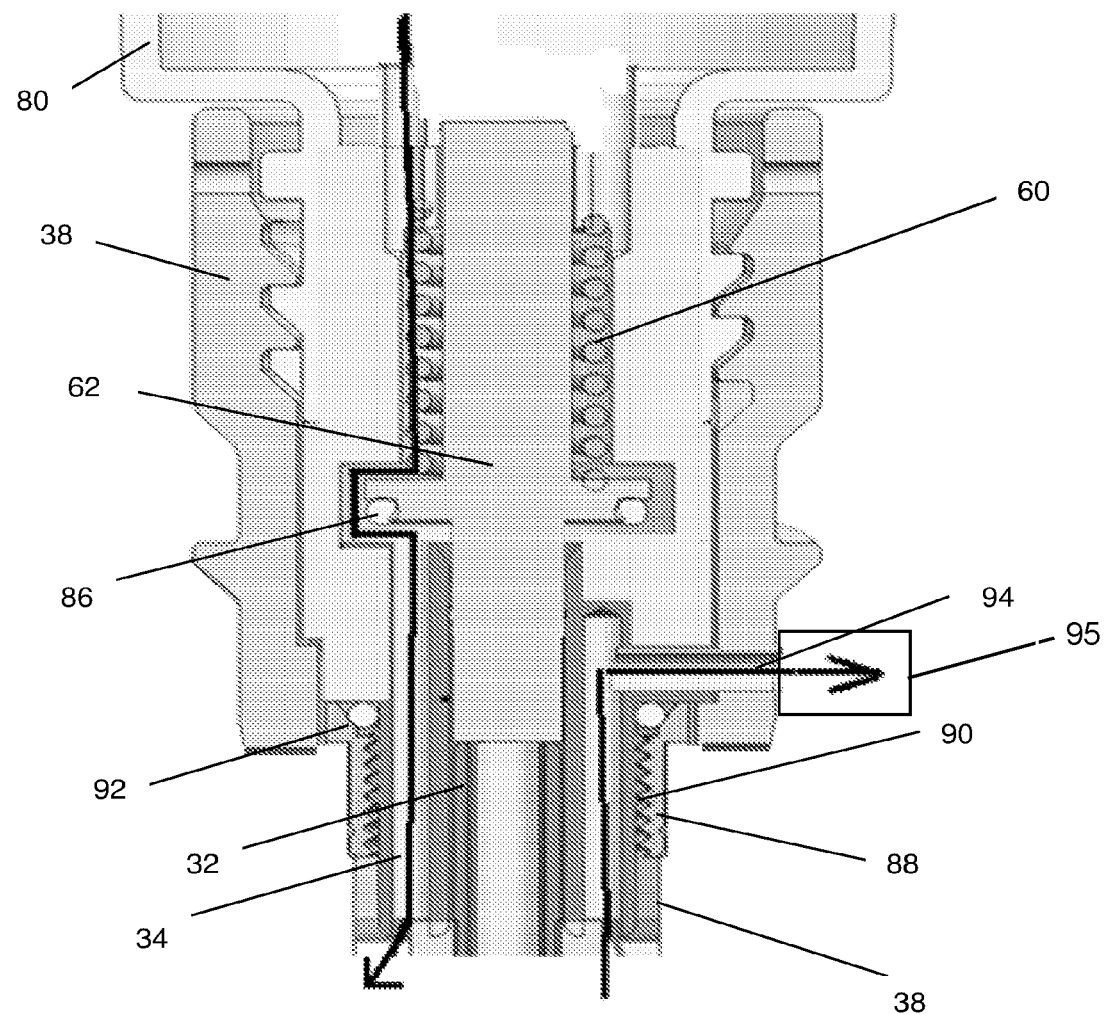
FIG. 9 is a cross-sectional view of the nozzle of the liquid dispenser of FIG. 8 inserted connected to a mouthpiece port at the end of the atomizer/liquid storage portion in a second configuration.

FIG. 9 illustrates the nozzle 38 fully engaged into the mouthpiece port 39 with the plunger 62 in an open configuration. In this configuration, the seal 86 provided on the plunger 62 is lifted away from the flow path through the nozzle 38 and therefore ceases to block the flow path and permits liquid to flow from the dispenser 80 into the liquid reservoir as indicted by the arrow on the left hand side of FIG. 9.

The relative lengths and arrangement of the plunger 62, air tube 32 and screw threads 88,90 are such that when the screw thread 90 of the nozzle 38 initially engages into the screw thread on the mouthpiece port 38, the end surface of the plunger 62 does not rest against the end of the air tube 32. Rather it is only when the screw threads 88, 90 are tightened to the extent which compresses the seal 92 (such as is illustrated in FIG. 9) that the plunger 62 reaches the end of the air tube 32. When this occurs as in the previous embodiment this pushes the plunger 62 against the coil spring 60 and opens a liquid flow path from the liquid dispenser 80 into the liquid reservoir 34 adjacent the air tube 32.

At the same time the seal 92 adjacent the screw thread 90 on the nozzle 38 is compressed sealing the end of the mouthpiece port 39, sealing the open entrance of the mouthpiece port 39. As with the first embodiment, with the plunger 62 in this position, the end of the air tube 32 within the liquid reservoir is capped by the plunger 62 which prevents liquid from entering the air tube 32 and flooding the atomizer 26 of the electronic cigarette.

In this embodiment, an air vent 94 separate from the liquid flow path is provided in the nozzle 38 enabling air to vent out of the liquid reservoir 34 as liquid is transferred into the liquid reservoir 34 from the liquid dispenser 80. The air flow path via the air vent 94 is indicated by the arrow on the right of the figure.

The present embodiment has a number of advantages over the first embodiment.

The provision of a seal 86 on the plunger 62 to block the liquid flow path from the liquid reduces the likelihood of the nozzle leaking prior to being attached to the atomizer/liquid storage portion 14 of an electronic cigarette.

Having the end of the plunger 62 recessed relative to the end of the nozzle 38 reduces the likelihood of accidental activation of the plunger 62.

Further by arranging the seal 92, and the screw threads 88 and 90 such that the plunger 62 only engages and is depressed by the end of the air tube 32 when the nozzle 38 is inserted into and attached to the atomizer/liquid storage portion 14 and the seal 92 is compressed, the possibility of leakage from the apparatus during the filling operation is reduced.

Finally, by providing an air vent 94 which is separate from the liquid flow path the flow of liquid is improved as the air vent 94 will not get blocked by liquid flowing into the liquid reservoir 34 preventing air from venting to atmosphere and resulting in a partial vacuum being generated within the apparatus disrupting liquid flow.

Third Embodiment

A third embodiment of the present invention will now be described.

Refilling an electronic cigarette with liquid for atomization involves a number of distinct stages. First the mouth piece 35 at the end of the electronic cigarette is removed, revealing the end of the liquid reservoir 34. Then a liquid dispenser 80 is utilized to fill the liquid reservoir 34. The liquid dispenser 80 is then removed and then finally the mouthpiece 35 is replaced.

In the previous two embodiments, refillable electronic cigarettes have been described in which a dispenser nozzle 38 is arranged to dispense liquid only when the nozzle 38 is engaged with the liquid reservoir 34 of an electronic cigarette. In the previous embodiments this is achieved by having the operation of the liquid dispenser activated by the engagement of a plunger 62 with the end of an air tube 32 of an electronic cigarette. This addresses the problem of accidental discharge of liquid from the liquid dispenser 80 other than when the liquid dispenser 80 is directed to filling an electronic cigarette.

In addition in the second embodiment by virtue of an arrangement of screw threads 88, 90 and a seal 92, a refilling system is described in which leakage of liquid during the refilling process is minimized.

However, even if accidental discharge of liquid for atomization is avoided and a liquid dispenser 80 and a liquid reservoir 34 are sealed during a refilling operation it is possible for liquid to leak from the liquid reservoir 34 either prior to attachment of the liquid dispenser 80 (if some residual liquid is present in the liquid reservoir 34 when the electronic cigarette is being refilled) or alternatively immediately after the liquid dispenser 80 has been detached from the electronic cigarette and prior to the reattachment of the mouthpiece 35.

In some electronic cigarettes, this problem is avoided by providing wadding, a sponge or other absorbent material within the liquid reservoir 34. However, in many electronic cigarettes the liquid reservoir 34 is in the form of an empty cavity or tank.

A third embodiment of the present invention will now be described in which the leakage of liquid for atomization from an electronic cigarette prior to or immediately after refilling the electronic cigarette and when the mouthpiece port 39 of the electronic cigarette is not enclosed by the presence of a mouthpiece 35 is prevented.

Figure 10:
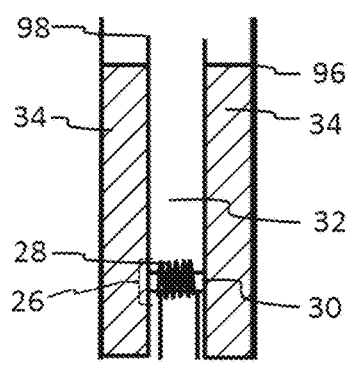
FIG. 10 is a schematic cross-sectional illustration of an atomizer and liquid reservoir for an electronic cigarette.

FIG. 10 is a schematic cross-sectional illustration of an atomizer and a liquid reservoir for an electronic cigarette. With the exception of a membrane 96 provided at the end of the liquid reservoir 34 adjacent the end 98 of the air tube 32, the structure of the atomizer/liquid reservoir is identical to the atomizer/liquid reservoir portion 14 of FIG. 1 and corresponding features have been identified with the same reference numerals as were used in relation to describing the atomizer/liquid reservoir portion 14 of FIG. 1.

Figure 11:
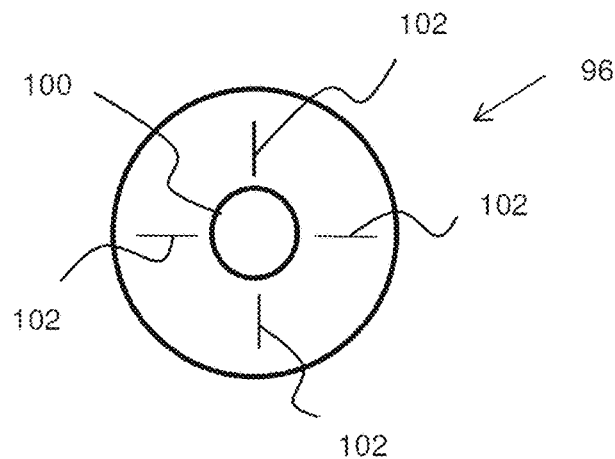
FIG. 11 is a plan view of a membrane for enclosing a liquid reservoir for an electronic cigarette.

FIG. 11 is a plan view of the membrane 96. In this embodiment the membrane comprises a circular disc of a rubber or other flexible material. A hole 100 is provided a the center of the disc with the hole corresponding in size with the size of the air tube 32 and the diameter of the disc corresponding in size to the opening at the end of the liquid reservoir 34. When positioned within the atomizer/liquid reservoir portion 14 the membrane acts to enclose the open end of the liquid reservoir 34 with the end 98 of the air tube 32 protruding through the hole 100 at the center of the disc. In the example illustrated 4 slit valves 102 are provided within the membrane 96. When the membrane 96 is in the position indicated in FIG. 10, these slit valves 102 will be in a closed configuration as is illustrated in FIG. 11. In this configuration the membrane acts as a barrier to prevent any liquid from within the liquid reservoir 34 from exiting the liquid reservoir 34.

Figure 12:
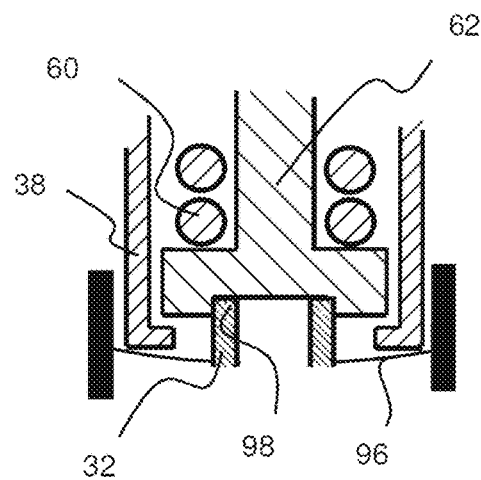
FIG. 12 is a schematic cross sectional illustration of a nozzle of a liquid dispenser engaging the membrane of FIG. 11.

FIG. 12 is a schematic cross sectional illustration of a nozzle 38 of a liquid dispenser engaging the membrane 96 of FIG. 11.

As in the previous embodiments, the nozzle 38 contains a plunger 62 which is biased by a spring 60 into a closed configuration in which liquid flow via the nozzle 38 is blocked. When the plunger 62 engages the end 96 of the air tube 32, this presses the plunger 62 against the spring 60 and opens a liquid flow path through the nozzle 38. At the same time, the plunger 62 caps the end 98 of the air tube 32 and prevents liquid from entering the air tube 32. In this embodiment, in addition, when the nozzle 38 is in this position, with the plunger 62 being engaging the air tube 32, the nozzle 38 presses against the membrane 96 causing the membrane 96 to deform.

Figure 13:
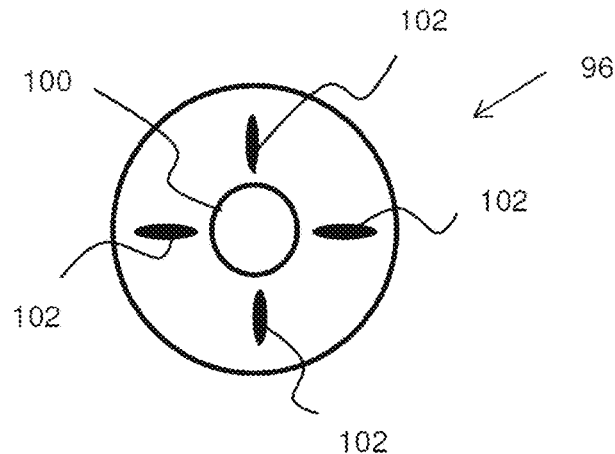
FIG. 13 is a plan view of the membrane of FIG. 11 in an open configuration.

FIG. 13 is a plan view of the membrane of FIG. 11 when the membrane 96 is deformed by the nozzle 38 pressing against the membrane 96. When deformed, the membrane 96 adopts an open configuration in which the slit valves 102 adopt an open configuration as is illustrated in the figure. In this configuration liquid passing via the fluid flow path within the nozzle 38 can enter the liquid reservoir 34 via the open slit valves 102.

However, when the nozzle 38 is withdrawn, the membrane 96 returns to the configuration shown in FIG. 11 where the slit valves 102 are closed and hence any liquid which has passed through the slit valves 102 into the liquid reservoir 34 is retained within the liquid reservoir 34.

Further Embodiments and Modifications

Although in the above embodiments a plunger 62 has been described as capping or blocking the end of an air tube 32 of an electronic cigarette, it will be appreciated that various alternative means for preventing liquid from entering the air tube 32 might be utilised. Thus for example rather than completely covering the end of the air tube, the plunger 62 might be shaped to deflect liquid away from the tube.

In the first embodiment the plunger 62 has been described as having a recess for capping the air tube 32 whereas a plunger 62 with a flat end surface is shown in the second embodiment. It will be appreciated that in other embodiments the end of the plunger might have a protrusion configured to enter into the air tube 32 to block the tube.

In the second embodiment a refilling system was described in where screw threads 88 were provided on the interior of a mouthpiece port 39 and on the exterior of a nozzle 39. It will be appreciated that other configurations of screw thread might be utilised. Thus for example a screw thread might be provided on the exterior or the mouthpiece port and a corresponding screw thread might be provided on an interior wall extending from the end of the nozzle 38.

It will also be appreciated that a number of different arrangements of a screw threads 88 and 90 and the plunger 62 and air tube 32 could be made which result in the plunger 62 only engaging with the end of the air tube 32 when the screw threads have engaged and preferably if a seal 92 is provided the seal 92 is compressed. Thus for example such arrangements would include recessing the plunger 62 relative to the end of the nozzle 38 bearing a screw thread 90 or recessing the end of the air tube 32 relative to the end of the mouthpiece port 39 bearing a screw thread 88 and in some embodiments both might be recessed.

In the second embodiment a refilling system has been described in which a liquid dispenser 80 is attached to a liquid reservoir 34 of an electronic cigarette via a pair of screw threads 88,90. It will be appreciated that other forms of connection such as magnetic, friction fit or push fit or bayonet fittings could be utilised instead.

It will also be appreciated that a seal 92 could be provided in the absence of any screw threads with arrangement of the seal 92 and the distances between the plunger 62 and the end of an air tube 32 being such that the seal 92 is caused be compressed prior to the plunger 62 being activated to open a liquid flow path between a liquid dispenser 80 and a liquid reservoir 34.

Instead of a spring 60 to provide the compression force on the plunger 62 to bias it into the closed position, alternative means of compression could be used. One example would be a flexible rubber material which is mildly compressed to bias the plunger 62, but with increased compression of the rubber material, the plunger 62 would move to the open position. Alternatively the rubber material could be assembled to be in tension when it is connected from the plunger 62 to the nozzle 38, and pushing/screwing the nozzle onto the atomiser results in an increase in tension to open the plunger.

Although in the second embodiment an air vent 94 has been described as enabling air to be vented to atmosphere, in other embodiments the air vent 94 could be connected to a low pressure air reservoir 95 such that air is caused to be sucked out of the liquid reservoir 34. In such embodiments low pressure air reservoir 95 might be activated by the operation of the plunger 62 so that air is sucked from the liquid reservoir 34 as liquid is delivered from the liquid dispenser.

Although in the above described embodiments nozzles 38 containing spring biased plungers 62 have been described as being attached to liquid dispensing bottles, it will be appreciated that such nozzles could be integrally formed with such dispensers or alternative could be attached to such dispensers. It will also be appreciated that other forms of liquid dispenser other than a bottle might be used to store liquid prior to transfer to a liquid reservoir 34 of an electronic cigarette or other electronic smoking device.

As noted in the introduction to this application, the dimensions of electronic cigarettes vary. It will therefore be appreciated that different electronic cigarettes may require nozzles of different sizes and or different arrangements of seals, screw threads and/or plungers might be required for refilling different types of electronic cigarette or other electronic smoking devices. It will therefore be appreciated that a liquid dispensing system could be provided with multiple detachable nozzles enabling the system to be adapted for use with different types and sizes electronic cigarettes and devices.

In the second embodiment a refilling system is described in which the flow of liquid is inhibited prior to a nozzle 38 being attached to the mouthpiece port 39 of an electronic cigarette by virtue of the relative arrangement of a plunger 62, an air tube 32 and the screw threads 80,90 provided on a nozzle 38 of a dispensing device and on the mouthpiece port 39 of an electronic cigarette. It will be appreciated that other means could be provided to inhibit fluid flow so as to avoid accidental discharge of liquid. Thus for example in some embodiments a protrusion might be provided on the exterior of the plunger 62 with a corresponding recess being provided within the cavity containing the plunger 62 (or vice versa) where the recess was blocked and user action was required remove the blockage (e.g. by depressing a button or twisting the device). A benefit of such a system would be that two actions (e.g. attaching the dispenser to the mouthpiece port 39 and depressing a button etc.) would be required to result in liquid being dispensed.

In the second embodiment a refilling system has been described in which a liquid dispenser 80 is attached to a liquid reservoir 34 of an electronic cigarette via a pair of screw threads 88,90. It will be appreciated that other forms of connection such as magnetic, friction fit or push fit or bayonet fittings could be utilised instead.

Although in the third embodiment a membrane 96 with four slit valves is illustrated, it will be appreciated that a membrane 96 with more or fewer slit valves 102 might be used. Similarly it will be appreciated that the arrangement of the slit valves 102 may differ from the arrangement illustrated in the figures.

Although in the above description, three embodiments have been described, it will be appreciated that aspects of the different embodiments could be combined. Thus for example the membrane 96 described in the third embodiment could be combined with the nozzles of the first or second embodiment. Similarly, the use of a seal 86 mounted on a plunger 86 as described in the second embodiment could be combined with the nozzle designs described in the other embodiments as could the presence of a second seal 92 on the nozzle 38 itself to improve the seal between a nozzle 38 and a port in an electronic cigarette used to refill the liquid reservoir of the electronic cigarette.

More generally, while this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

The invention claimed is:

1. A liquid supply system for an electronic smoking device comprising:
    a liquid dispenser;
    a nozzle; and
    a liquid reservoir of the electronic smoking device;
    wherein the nozzle comprises:
        a housing defining a liquid flow path through the nozzle; and
        a plunger provided within the liquid flow path, the plunger being moveable between an open position in which liquid may flow through said liquid flow path and a closed position in which liquid flow through said liquid flow path is restricted wherein the plunger is biased towards said closed position; wherein nozzle and plunger are configured so that when the nozzle is inserted into an engagement position within an opening providing access to the liquid reservoir of the electronic smoking device which contains an air tube for extracting vapour from the electronic smoking device, the plunger engages with said air tube and is moved from said closed position to said open position, the plunger in said engagement position being such as to divert liquid flowing via the liquid flow path through said nozzle into the liquid reservoir and away from the air tube,
    wherein
    an air vent is provided enabling air to vent from the liquid reservoir when the nozzle is in said engagement position within the opening within an electronic smoking device;
        wherein the air tube for extracting vapour from the electronic smoking device is accessible via said opening; and
        wherein a membrane having one or more slit valves is provided adjacent the end of the air tube accessible via said opening, wherein when said nozzle is in said engagement position, said membrane is caused to be deformed opening said slit valves and permitting liquid to flow into said liquid reservoir.

2. A liquid supply system in accordance with claim 1, wherein said plunger comprises a sealing surface adapted to engage with and block the air tube of the electronic smoking device when the nozzle is in the engagement position, preventing liquid flowing via the liquid flow path through the nozzle from entering said air tube.

3. A liquid supply system in accordance with claim 1, wherein a sealing member is mounted on said plunger, wherein said sealing member seals said liquid flow path when said plunger is in said closed position.

4. A liquid supply system in accordance with claim 1, wherein a sealing member is mounted on said nozzle wherein said sealing member is configured to seal the opening.

5. A liquid supply system in accordance with claim 4, wherein said nozzle is configured so that said sealing member seals the opening prior to the air tube of the electronic smoking device engaging with the plunger and moving the plunger into an open position.

6. A liquid supply system in accordance with claim 1, wherein a screw thread, bayonet, magnetic, friction fit, push fit or other type of fitting is provided on said nozzle which matches a corresponding screw thread, bayonet, magnetic, friction fit, push fit or other type of fitting at the opening providing access to the liquid reservoir.

7. A liquid supply system in accordance with claim 6, wherein the screw thread, bayonet, magnetic, friction fit, push fit or other type of fitting is positioned on said nozzle so that if the nozzle is attached to a device having a matching screw thread, bayonet, magnetic, friction fit, push fit or other type of fitting, said screw thread, bayonet, magnetic, friction fit, push fit or other type of fitting engage each other before the plunger engages with the air tube within said opening.

8. A liquid supply system in accordance with claim 1, wherein said air vent is connected to a low pressure reservoir arranged to extract air from the liquid reservoir when said nozzle is in the engagement position.

9. A liquid supply system in accordance with claim 8, wherein said low pressure reservoir is activated by movement of said plunger to extract air from the liquid reservoir when said plunger is in said open position.

10. A liquid supply system in accordance with claim 1, wherein said plunger has an indentation operable to receive the air tube of an electronic cigarette when said nozzle is in the engagement position.

11. A liquid supply system in accordance with claim 1, wherein said plunger is biased towards said closed position by a spring.

12. A liquid supply system in accordance with claim 1, wherein movement of the plunger from said closed position to said open position compresses a resilient material, the compression of said resilient material biasing said plunger towards said closed position.

13. A liquid supply system in accordance with claim 1, wherein movement of the plunger from said closed position to said open position stretches a resilient material attached to said plunger, the stretching of said resilient material biasing said plunger towards said closed position.

14. A liquid supply system for an electronic smoking device in accordance with claim 1, wherein said opening is a mouthpiece port operable to receive a mouthpiece configured for extracting vapour via said air tube.

15. A liquid reservoir for an electronic smoking device comprising:
    a body portion having a central cavity accessible via an opening;
    an air tube for extracting vapour from an electronic smoking device provided within said central cavity, accessible via said opening; and
    a membrane having one or more slit valves provided adjacent the end of the air tube accessible via said opening;
    wherein said membrane is configured to be deformed to open said slit valves and permit liquid to flow into said central cavity.

16. A liquid reservoir in accordance with claim 15, wherein said opening is a mouthpiece port operable to receive a mouthpiece configured for extracting vapour via said air tube.

17. A liquid reservoir in accordance with claim 16, further comprising an atomizer operable when connected to power supply to atomize liquid stored in the liquid reservoir.

* * * * *